United States Patent
Kang et al.

(10) Patent No.: US 10,751,030 B2
(45) Date of Patent: Aug. 25, 2020

(54) ULTRASOUND FUSION IMAGING METHOD AND ULTRASOUND FUSION IMAGING NAVIGATION SYSTEM

(71) Applicants: SHENZHEN MINDRAY BIO-MEDICAL ELECTRONICS CO., LTD., Shenzhen (CN); Tsinghua University, Beijing (CN)

(72) Inventors: Jingang Kang, Beijing (CN); Guangzhi Wang, Beijing (CN); Lei Zhu, Beijing (CN); Qian Zhang, Beijing (CN); Hui Ding, Beijing (CN); Minglei Yang, Beijing (CN); Longfei Cong, Beijing (CN)

(73) Assignees: SHENZHEN MINDRAY BIO-MEDICAL ELECTRONICS CO., LTD., Shenzhen (CN); TSINGHUA UNIVERSITY, Beijing (CN)

( * ) Notice: Subject to any disclaimer, the term of this patent is extended or adjusted under 35 U.S.C. 154(b) by 748 days.

(21) Appl. No.: 15/094,821

(22) Filed: Apr. 8, 2016

(65) Prior Publication Data

US 2017/0020489 A1 Jan. 26, 2017

Related U.S. Application Data

(63) Continuation of application No. PCT/CN2014/074451, filed on Mar. 31, 2014.

(30) Foreign Application Priority Data

Oct. 9, 2013 (CN) .......................... 2013 1 0468271

(51) Int. Cl.
*A61B 8/08* (2006.01)
*A61B 8/00* (2006.01)
(Continued)

(52) U.S. Cl.
CPC .............. *A61B 8/5284* (2013.01); *A61B 5/08* (2013.01); *A61B 8/0866* (2013.01);
(Continued)

(58) Field of Classification Search
CPC ....... A61B 8/5284; A61B 5/08; A61B 8/0866; A61B 8/4254; A61B 8/463; A61B 8/5238;
(Continued)

(56) References Cited

U.S. PATENT DOCUMENTS 6,501,981 B1 * 12/2002 Schweikard ........... A61B 6/527
600/427
8,126,239 B2 * 2/2012 Sun .......................... A61B 6/12
382/131
(Continued)

FOREIGN PATENT DOCUMENTS

CN 101983035 A * 2/2011 ............. A61B 5/113
CN 103123721 A 5/2013
(Continued)

OTHER PUBLICATIONS

Wein, W., Cheng, J., and Khamene, A., Ultrasound based respiratory motion compensation in the abdomen, 2008, In: Worshop on Image Guidance and Computer Assistance for Softissue Intervetions, MICCAI, vol. 32, No. 6, p. 294.*
(Continued)

*Primary Examiner* — Amanda Lauritzen Moher
(74) *Attorney, Agent, or Firm* — Kory D. Christensen

(57) ABSTRACT

The present application relates to an ultrasound fusion imaging method and an ultrasound fusion image navigation system. The ultrasound fusion imaging method includes a selection step, a registration step and a fusion step. The selection step is for selecting at least one ultrasound image from at least one previously stored piece of ultrasound video
(Continued)

data according to an input instruction. The ultrasound video data includes an ultrasound image obtained by acquiring a target object in at least one plane and position indicating information corresponding to the ultrasound image. The registration step is for registering the selected at least one ultrasound image with a modality image. The registration process uses the location of the position indicating information of the at least one ultrasound image. The fusion step is for fusing the registered ultrasound image with the modality image.

9 Claims, 6 Drawing Sheets

(51) Int. Cl.
  G16H 50/00 (2018.01)
  G16H 50/50 (2018.01)
  A61B 5/08 (2006.01)
  A61B 90/00 (2016.01)
(52) U.S. Cl.
  CPC .......... *A61B 8/4245* (2013.01); *A61B 8/4254* (2013.01); *A61B 8/463* (2013.01); *A61B 8/5238* (2013.01); *A61B 8/5246* (2013.01); *A61B 8/5261* (2013.01); *A61B 8/5276* (2013.01); *G16H 50/00* (2018.01); *G16H 50/50* (2018.01); *A61B 2090/365* (2016.02)
(58) Field of Classification Search
  CPC ... A61B 8/5246; A61B 8/5261; A61B 8/5276; A61B 2090/365; A61B 2090/367; A61B 8/08; G16H 50/00; G16H 50/50
  USPC .................................................. 600/440, 424
  See application file for complete search history.

(56) References Cited

U.S. PATENT DOCUMENTS

| | | | | |
|---|---|---|---|---|
| 8,989,349 | B2* | 3/2015 | Thomson | A61B 6/037 378/65 |
| 2001/0035871 | A1* | 11/2001 | Bieger | A61B 5/065 345/630 |
| 2005/0180544 | A1 | 8/2005 | Sauer et al. | |
| 2005/0197559 | A1* | 9/2005 | Boese | A61B 5/0073 600/407 |
| 2006/0020204 | A1* | 1/2006 | Serra | A61B 8/0833 600/437 |
| 2006/0262970 | A1 | 11/2006 | Boese et al. | |
| 2007/0010743 | A1* | 1/2007 | Arai | A61B 8/13 600/443 |
| 2007/0015991 | A1* | 1/2007 | Fu | A61B 8/08 600/407 |
| 2007/0270689 | A1* | 11/2007 | Lothert | A61B 6/032 600/428 |
| 2009/0182224 | A1* | 7/2009 | Shmarak | A61B 5/7275 600/424 |
| 2009/0276245 | A1* | 11/2009 | Cziria | G06Q 10/06 705/3 |
| 2010/0145197 | A1* | 6/2010 | Stapf | A61B 5/416 600/445 |
| 2010/0290683 | A1* | 11/2010 | Demeester | A61B 6/037 382/131 |
| 2010/0324409 | A1* | 12/2010 | Assmann | A61B 5/055 600/410 |
| 2011/0224550 | A1* | 9/2011 | Shinohara | A61B 8/00 600/443 |
| 2013/0172730 | A1* | 7/2013 | Cohen | A61B 6/12 600/424 |
| 2013/0172739 | A1* | 7/2013 | Paladini | A61B 6/4258 600/436 |
| 2013/0303898 | A1* | 11/2013 | Kinahan | A61B 6/481 600/425 |
| 2014/0193053 | A1* | 7/2014 | Kadoury | G06T 15/08 382/131 |
| 2015/0051489 | A1* | 2/2015 | Caluser | A61B 8/0825 600/440 |

FOREIGN PATENT DOCUMENTS

| | | | | |
|---|---|---|---|---|
| CN | 103230283 A | | 8/2013 | |
| WO | WO 2008065600 A2 * | | 6/2008 | ........... G06T 3/0081 |
| WO | WO 2012117381 A1 * | | 9/2012 | ........... G06T 11/008 |

OTHER PUBLICATIONS

Borgert, J., Kruger, S., Timinger, H., Krucker, J., Glossop, N., Durrarni, A., Viswanathan, A., and Wood, B. J., Respiratory motion compensation with tracked internal and external sensors during CT-guided procedures, May 2006, Comput Aided Surg., vol. 11, No. 3, pp. 119-125.*

Penney, G., Blackall, J., Hamady, M., Sabharwal, T., Adam, A., and Hawkes, D., Registration of freehand 3D ultrasound and magnetic resonance liver images, 2004, Med. Image Anal., vol. 8, pp. 81-91.*

Huang, X., Moore, J., Guiraudon, G. Jones, D. L., Bainbridge, D. Ren, J., and Peters, T. M., Aug. 2009, Dynamic 2D ultrasound and 3D CT image registration of the beating heart, IEEE Trans. of Medical Imaging, vol. 28, No. 8, pp. 1179-1189.*

King, D., King Jr., D. L. and Shao, M. Y., Three-dimesional spatial registration and interactive display of position and orientation of real-time ultrasound images, 1990, J Ultrasound Med., vol. 9, pp. 525-532.*

Wollny, G., Ledesma-Carbayo M. J., Kellman, P., and Santos, A, Non-Rigid motion compensation in free breathing myocardial perfusion magnetic resonance imaging, 2008, Computers in Cardiology, vol. 35, pp. 465-468.*

Xu, S., Kruecker, J., Turkbey, B., Glossop, N., Singh, A. K., Choyke, P., Pinto, P., and Wood. B. J., Real-time MRI-TRUS fusion for guidance of targeted prostate biopsies, 2008, Computer Aided Surgery, vol. 13, No. 5, pp. 255-264.*

Harvtov, A., Eisner, S. D., Roberts, D. W., Paulsen, K. D., Platenik, L. A., and Miga, M. I., Error analysis for a free-hand three-dimensional ultrasound system for neuronavigation, 1999, Neurosurg Focus, vol. 6 No. 3, Article 5.*

Penney, G.P., Barratt, D.C., Chan, C.S.K., Slomczykowski, M., Carter, T.J., Edwards, P.J., and Hawkes, D.J., Cadaver validation of intensity-based ultrasound to CT registration, 2006, Med. Image Anal., vol. 10, pp. 385-395.*

Sun, Y., Kadoury, S., Li, Y., John, M., Resnick, J., Plambeck, G., Liao, R., Sauer, F., Xu, C., 2007, Image guidance of intracardiac ultrasound with fusion of pre-operative images, In: International Conference on Medical Image Computing and Computer-Assisted Intervention (MICCAI), 10, pp. 60-67.*

Sato, Y., Nakamoto, M., Tamaki, T., Sasama, T. Sakita, I., Nakajima, Y., Monden, M., and Tamura, S., Image guidance of breast cancer surgery using 3-D ultrasound images and augmented reality visualization, Oct. 1998, IEEE Transactions on Medical Imaging, vol. 17, No. 5, pp. 681-693.*

Zhu, L., Wenjun, L., Ding, H., Zhu, L., and Wang, G. Towards an accurate ultrasound image fusion system, Aug. 2011, The 7th Asian Conference on Computer Aided Surgery (ACCAS 2011).*

Zhu, L., Ding, H., Zhu, L. Wang, G., A robust registration method for real-time ultrasound image fusion with pre-acquired 3D dataset, Aug. 30-Sep. 3, 2011, 33rd Annual International Conference of the IEEE EMBS. pp. 2638-2641.*

Gruber, D., The mathematics of 3D rotation matrix, Sep. 30-Oct. 1, 2000, Xtreme Game Developers Conference, Santa Clara, California URL: http://fastgraph.com/makegames/3drotation/.*

Giachetti, A., Matching techniques to compute image motion, 2000, Image and Vision Computing, vol. 18, pp. 247-260.*

(56) References Cited

OTHER PUBLICATIONS

Wollny, G., Ledesma-Carbayo, M. J., Kellman, P., and Santos, A. Exploiting quasiperiodicity in motion correction of free-breathing myocardial perfusion MRI, Aug. 2010, IEEE Transactions on Medical Imaging, vol. 29, No. 8, pp. 1516-1527.*

Nakamoto, M., Hirayama, H., Sato, Y., Konishi, K. Kakeji, Y., Hashizume, M. and Tamura, S. "Recovery of respiratory motion and deformation of the liver using laparoscopic freehand 3D ultrasound system," 2007, Medical Image Analysis, vol. 11, pp. 429-442.*

Gierga D., Brewer, J., Sharp, G., Betke, M., Willett, C., and Chen, G., "The correlation between internal and external markers for abdominal tumors: implications for respiratory gating," 2005, Int. J. Radiation Oncology Biol. Phys., vol. 61, No. 5, pp. 1551-1558.*

Ernst, F., Bruder, R., Schlaefer, A., and Schweikard, A., "Correlation between external and internal respiratory motion: a validation study," 2012, Int J CARS, vol. 7, pp. 483-492.*

Blackall, J., Penney, G., King, A. and Hawkes, D., "Alignment of sparse freehand 3-D ultrasound with preoperative images of the liver using models of respiratory motion and deformation," 2005, IEEE Transactions on Medical Imaging, vol. 24, No. 11. pp. 1405-1416.*

He, T., Xue, Z., Xie, W., and Wong, S., "Online 4-D CT Estimation for Patient-Specific Respiratory Motion Based on Real-Time Breathing Signals," 2010, In: Medical image computing and computer-assisted intervention—MICCAI 2010, Springer, New York, pp. 392-399.*

Xu et al.,"A novel respiratory detection method based on automated analysis of ultrasound diaphragm video", 2006, Medical Physics, vol. 33, No. 4, pp. 916-921 (Year: 2006).*

* cited by examiner

ULTRASOUND FUSION IMAGING METHOD AND ULTRASOUND FUSION IMAGING NAVIGATION SYSTEM

TECHNICAL FIELD

The present disclosure relates to medical ultrasound imaging, in particular to fusion methods for fusing ultrasound images with a pre-stored modality image and an ultrasound fusion imaging navigation system.

BACKGROUND

More than one kind of image-generating system for sampling target object is able to be implemented in clinical, so that doctor can acquire multiple models of medical images, such as Computed Tomography (CT), Magnetic Resonance (MR) or ultrasound image. The principle of ultrasound image fusion navigation is, through space positioning devices (usually Magnetic locating sensor fixed on a probe), to built a spatial corresponding relation to real-time ultrasound images with other pre-acquired modality data (such as CT or MR image) and display the overlapped cutting sections images with the pre-acquired modality data for achieving the fusion of above two kinds of images. Under above, these two kinds of images are used both in diagnosis process and treatment process to combine the high resolutions feature of CT or MR with the real-time feature of ultrasound image so as to provide more detail diagnosis information for doctor in clinical to increase the effect of treatment.

In the ultrasound image fusion navigation system, the most important technique point is to register ultrasound images with the modality data. In detail, the practice of above registering point is to map the position of the point (or plane) of the ultrasound images in a world coordinate system with the position of the point (or plane) of the modality image in a world coordinate system correspondingly. Acquiring target position in the world coordinate system precisely is in significant effect for increasing the accuracy of registration.

The conventional registration technique is based on real-time ultrasound detection; doctor acquires ultrasound images for providing registering information by freezing the present frame. This kind of method, processing the real-time ultrasound image frame by frame, is well known for those skilled in the art. In addition, if doctor wants to acquire certain section image in certain breath depth, patient usually is asked to cooperate by precisely controlling his breath. Especially, when image fusion of abdominal organs for those patients, who's breath way is in abdominal breath way, is conducted, huge errors is generated because of the movement, rotation and deformation caused by the abdominal breath of patient. Therefore, patient is asked to precisely controlling his breath. It raises the requirements for both doctor and patient. If patient cannot control his breath well enough or doctor has a lack of experience, the effect is usually not satisfied so as to reduce the accuracy of registration and the successes rate for image fusion. Right now, the method for eliminating breath effect is depending on doctor's decisions by manually determining breath phase or adding a sample sensor for sample breath control. However, the performances of above solutions are all poor and unsatisfied.

SUMMARY

Therefore, an ultrasound fusion imaging method and an ultrasound imaging navigation system for eliminating or reducing breath effect are provided.

A method for fusing at least one ultrasound image and a pre-stored modality image comprises a selection step, a registration step and a fusion step. The selection step is for selecting at least one frame of ultrasound image from at least one pre-stored ultrasound video data according to an input instruction. The ultrasound video data comprises ultrasound images acquired by sampling a target object from at least one plane and position-indicating information corresponding to each of the ultrasound images. The position-indicating information is generated by a position sensor, fixed with an ultrasonic probe, according to a motion state of the ultrasound probe sensing by the position sensor during the acquisition of the ultrasound images. The registration step is for registering the selected at least one ultrasound image with the modality image. The at least one position-indicating information is implemented in above registering process. The fusion step is for fusing the registered at least one ultrasound image with the modality image.

In one embodiment of the method for fusing at least one ultrasound image and pre-acquired modality image of the present invention, multiple frames of ultrasound images are selected in the selecting step. The method further comprises a breath model built step and a breath-correcting step. The breath model built step is for building a breath model according to the ultrasound video data. The breath-correcting step is conducted before the registering step or during the fusion step for implementing the breath model to correct the multiple frames of ultrasound images into the same breath depth level.

A method for fusing at least one ultrasound image with a pre-stored modality image including a selection step, a breath model built-up step, a registering step and a fusion step is provided.

The selection step is for selecting multiple frames of ultrasound images from at least one portion of ultrasound video data. The ultrasound video data comprises ultrasound images acquired by sampling the target object from at least one plane and position-indicating information corresponding to each frame of the ultrasound images. The position-indicating information is generated by a position sensor fixed with an ultrasonic probe while acquiring the ultrasound images.

The breath model built-up step is for building a breath model according to the ultrasound video data;

The registering step is for registering the multiple frames of ultrasound images with the modality image;

The fusion step is for fusing the registered multiple frames with the modality image. The breath model is implemented to correct the multiple frames of the ultrasound images into the same breath depth before the registering step or in the fusion step.

An ultrasound fusion imaging navigation system, comprises: an ultrasound probe and a position sensor fixed with the probe; a sampling module implemented for sampling the target object from at least one plane to generate at least one ultrasound video data comprising registering information and storing position-indicating information for each frame of ultrasound images in each ultrasound video data, wherein position indicating information is generated by the position sensor according to motion of the ultrasound probe in the acquiring process of the ultrasound images; a replaying module for replaying the pre-stored ultrasound video data according to an input instruction; a selecting module for selecting at least one frame of the ultrasound images from the replaying ultrasound video data according to a selection instruction; a registering module for registering the selected at least one frame of ultrasound images with a modality image, wherein the position-indicating information of the at least one ultrasound images is implemented in above registering process; and a fusion module for image fusing the registered ultrasound images with the modality image.

A distinct image fusion method comparing with conventional real-time base fusion method is implemented by the ultrasound fusion imaging method and an ultrasound imaging navigation system of the present invention. The fusion method disclosure in the present invention comprises a step of sampling the target subject and pre-recording a video data accordingly before the registering process, and selecting one or multiple ultrasound images thereafter. Therefore, the performance for reducing the target object breath effect in the embodiment of the present invention is significantly increased.

DETAILED DESCRIPTION

Specific details for fully understanding each of embodiments and implemented by those skilled in the art are provided in the below description. However, it should be understood for those skilled in the art that the present invention is able to be implemented without the specific details as well. In some embodiments, conventional structures and functions are omitted to avoid confusions in the descriptions of the embodiments.

Unless it is acquired clearly under context of the descriptions, the terms "comprise", "include" should be defined as opening definition but not limited or exhaustive definition.

Figure 1:
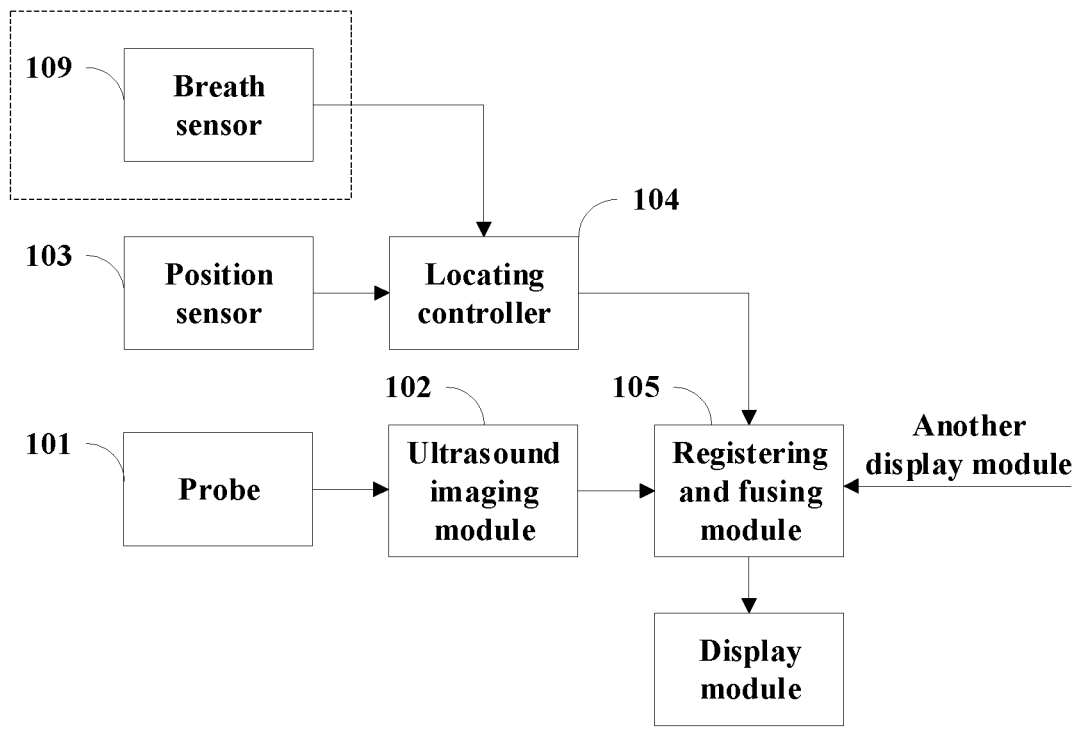
FIG. 1 is a schematic block diagram of an ultrasound fusion imaging navigation system in accordance with an embodiment of the present disclosure.

A schematic block diagram of ultrasound image fusion navigation system is shown in FIG. 1. An ultrasound probe 101 emits ultrasound to at least one target organ of human body. An ultrasound imaging module 102 is implemented for received echo wave signal of the ultrasound emitting from the ultrasound probe 101 to generate at least one ultrasound image of the target organ. At least one pre-stored modality image, such as CT image or MR image, is imported into a registering fusion module 105. A position sensor 103 fixed with the ultrasound probe 101 senses position of the probe 101 and provides position information constantly along with motion of the ultrasound probe 101. The position information comprises information relating to 6-axises space position information of the ultrasound probe 101 (including but not limiting to vertical direction, horizontal direction, portrait direction, pitch direction, roll direction and sway direction-). The registering and fusion module 105 registers and fuses the ultrasound image with a modality image by implementing the image information and the position information.

Figure 2:
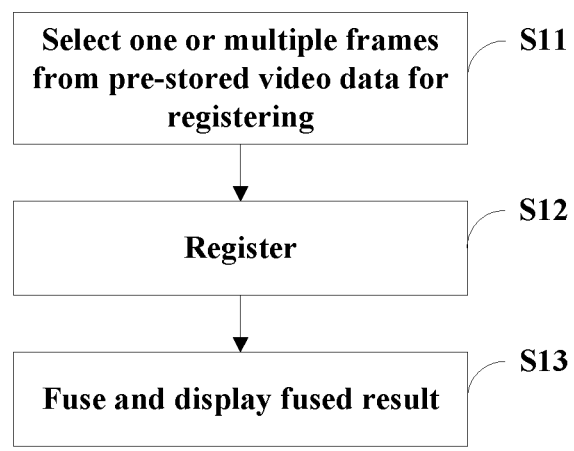
FIG. 2 is a schematic flow chart of a fusion method for fusing ultrasound images with a pre-stored modality image in accordance with an embodiment of the present disclosure.

Combining with the ultrasound image fusion navigation system shown in FIG. 1, a schematic flow chart of a fusion method of the ultrasound image and pre-stored modality image is provided and shown as FIG. 2, comprising step S11 to S13 as disclosed below: a selection step S11, selecting at least one frame of ultrasound image from a pre-stored ultrasound video data according to an input instruction.

The pre-stored ultrasound video data comprises pre-sampling data of target object (target organ, such as liver) so as to generate built-in registering information (registering video). Position indicating information $R_{probe}(t)$, which relates to position of the position sensor 103 fixing with the ultrasound probe 101, is recorded synchronically for each frame of ultrasound images t. The position-indicating information $R_{probe}(t)$ is generated by the position sensor 103 fixing with the ultrasound probe 101 according to the motion state of the ultrasound probe 101 in the process of acquiring the ultrasound images. It means, the content in the registering video data comprises at least both the ultrasound images data and the position-indicating information $R_{probe}(t)$ of the position sensor 103 in addition. In one embodiment, the position sensor 103 is capable of applying as an electromagnetic induction base position sensor, or an optical base position sensor as well. An acoustics base position sensor is also able to be applied into this embodiment. For explaining the present invention but not as limitations, electromagnetic induction base position sensor is implemented for describing in below embodiments of this application.

In the selection step, the input instruction is capable of selecting from external user input, or automatically triggering the instruction inside the system when the registering and fusing is processed. In one embodiment, the pre-stored ultrasound video data is replayed, and the selection step is conducted thereafter in above replaying process. Commands for playing and selecting the ultrasound video data are determined under user's demands. Embodiments of how to play and select the ultrasound video data are able to be implemented under conventional technologies, just only needs to satisfy functions suitable for replaying ultrasound video data and selecting image frames. In above ultrasound replaying step, the pre-stored ultrasound video data could be replayed one frame by another, from beginning to the end, or could be directly dragged to a specific frame containing valuable target organ cutting-section image via program tool bar or mechanical switch button. In another embodiment, the ultrasound video data is also selected under pre-determined conditions, for example, some specific frames such as 20 frames ahead in the ultrasound video data are capable of being predetermined to be selected.

In the registering step S12, at least one selected ultrasound image frame is registered with the modality image wherein the position indicating information of the corresponding ultrasound image frames are implemented in this step in the mean time.

In various embodiments, the three dimensional ultrasound imaging system may scan the head of a fetus, i.e., may transmit ultrasound waves towards the head of the fetus and receive ultrasound echoes, to obtain ultrasound echo signals.

The ultrasound echo signals may be processed as described above and thereby three dimensional amount data of the head of the fetus (hereinafter, "three dimensional amount data") may be obtained. The specific processes for scanning the target and processing the ultrasound echo signals to obtain the three dimensional amount data can be the same to or similar with those which are well known in the art and thus will not be described in details herein.

For the purposes of increasing total accuracy of the system, two or more ultrasound image frames in the modality image are selected in the registering step S12 in another embodiment. It should be noticed that multiple frames of ultrasound images can only be applied in the registering step S12 only on the condition that above ultrasound images frames are sampled under the same or similar breath state (depth). Generally, if ultrasound images frames are all sampled under the state when patient temporally stops his breath, each ultrasound image frame of the video data should be considered under similar breath state so as could be directly applied to register at the same time in the registering step S12.

Figure 3:
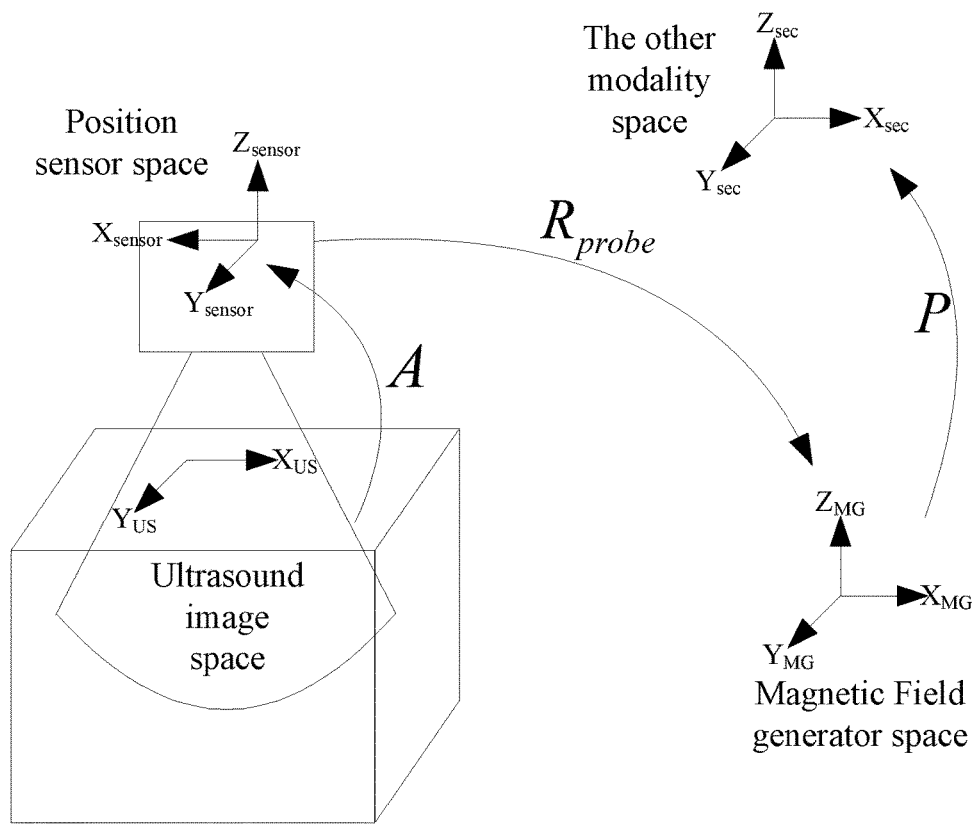
FIG. 3 is a schematic block diagram of spatial switching in accordance with an embodiment of the present disclosure.

In the registering step S12, a spatial transformation algorithm is implemented for mapping one image to a frame image so that each pixel of above two images corresponding to the same position in one space coordinate system could be linked correspondingly. Therefore, above image information could be fused with corresponding images correctly. Under above described algorithm, in the ultrasound image fusion navigation system of the present invention, the registration process for the ultrasound image and the modality image could be implemented via a spatial transformation reference shown in FIG. 3. In the other word, each pixel of the ultrasound images is transformed from the coordinate system of its own to the coordinate system of the position sensor 103 at first, and then transformed from the coordinate system to World Coordinate System (WCS) thereafter. In the end, each pixel of the ultrasound images is transformed from WCS to the coordinate system of the modality image. In this and other embodiments, WCS means a reference coordinate system, which is definable under requirements, such as a coordinate system of a magnetic field generator or other coordinate system is also applicable for sure. The spatial transformation reference shown in FIG. 3 could be described as a mathematical formula formation:

$$X_{sec} = P \cdot R_{probe} \cdot A \cdot X_{us} \quad (1)$$

Wherein, $X_{us}$ is the coordinate of one position in the ultrasound image, $X_{sec}$ is the coordinate indicating to the same position in the modality image, A is a transformation vectors matrix from the ultrasound image space coordinate system to the position sensor space coordinate system, $R_{probe}$ is a transformation vectors matrix from the space coordinate system of the position sensor to the space coordinate system of the magnetic field generator, P is a transformation vectors matrix from the reference coordinate system to the space coordinate system of the modality image.

Regarding to the configuration of the transformation vectors matrix A, since the position sensor 103 is fixed with the ultrasound probe 101, when the ultrasound probe 101 is hold in a constant depth, the transformation vectors matrix A is fixed as well. Therefore, the transformation vectors matrix A is acquirable through calibration algorithm by combining the position indicating information $R_{probe}(t)$ before registering.

Regarding to the configuration of $R_{probe}$, it could be directly accessed from a locating controller 104 electrically connected with the position sensor. In this embodiment, $R_{probe}$ is varying constantly with the motion of the ultrasound probe 101.

Regarding to the configuration of P, which is also defined as registration matrix, could be acquired by applying formula (1) via finding corresponding point or plane between the coordinate spaces of the ultrasound image and the modality image. In one embodiment, some specific point or area of the target organ are marked. Above marked point or area of the target organ are sampled to generate at least one point or area $X_{us}$ in the coordinate space of the ultrasound image and at least one point or area $X_{sec}$ in the coordinate space of the modality image so as to generate P from above through applying Formula (1). In another embodiment, some points or areas of the coordinate space of the ultrasound image are transformed to WCS, and some points or areas of the coordinate space of the modality image are also transformed to WCS thereafter so that $X_{sec}$ in the coordinate space of the modality image, corresponding to $X_{us}$ in the coordinate space of the ultrasound image, is acquired through image mapping algorithm. Thereafter, P is generated from $X_{sec}$ and $X_{us}$. For those skilled in the art of this field, it is easy to reach that a reversing transformation algorithm could be applied to acquire a reversing coordinate transformation from one coordinate space of image to another.

In step S13, image fusion is conducted between the registered ultrasound image and the modality image. Above image fusion step could be implemented by referring to conventional image fusion algorithm, such as image fusion based on empty space algorithm, maximum (minimum) gray-scale value algorithm, weighted gray-scale value algorithm, or image fusion based on domain transformation, such as multi-resolution pyramid algorithm or Fourier transformation.

Under above steps, the ultrasound images and the modality image are registered and fused. The implemented image fusion algorithm here is different from conventional applications. In detailed, conventional application is based on real-time ultrasound process of dealing (freezing) frames one by one. On the other hand, the embodiment is implemented by recording (pre-stored) a video data before the registering S12 step then selecting one or more frames of the video data for registering via replaying the video data.

Figure 4:
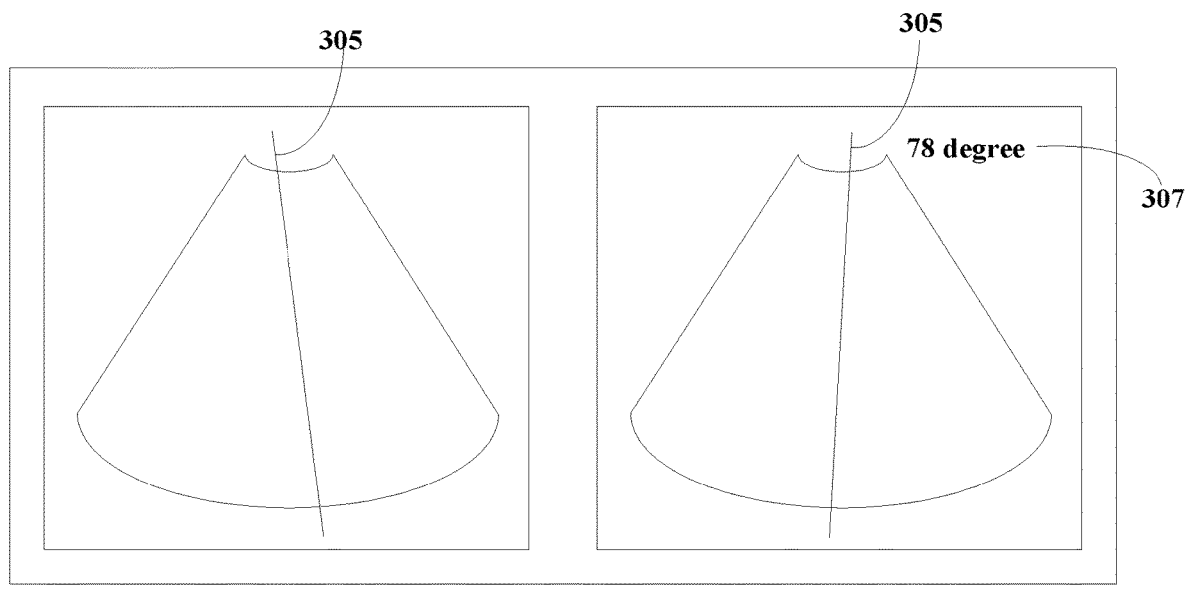
FIG. 4 is a schematic block diagram for displaying multiple registering planes in accordance with an embodiment of the present disclosure.

Except above steps, the image fusion method for fusing the ultrasound image and the modality image further comprises below steps: a multi-frames displaying step, displaying intersection lines and included angles among these frames at the time when the multi-frames are registered or fused. As shown in FIG. 4, an intersection lines position 305 among different frames of the ultrasound images and an included angle 307 between two frames are illustrated in the right block and the left block individually. If displaying of multiple registered or fused frames is needed, it could be implemented by selecting one of the multiple frames as a reference frame and defined its intersection lines and the included angle as intersection lines and included angle among each of the remaining frames and the reference frame. One of the advantages in this embodiment is relative positions among the frames are indicated more intuitively so as to increase performance for the registering step S12 thereafter.

The breath-controlling ability of many patients is usually lower than its normal state when the ultrasound image fusion navigation system is implemented. On the other hand, the pre-stored video data for registering is sampled and fused when the breath-controlling ability of the patients is under normal and free condition. Therefore, the effect caused under different breath conditions of patients in registering and fusing processes are significant and should be reduced or eliminated, because complex motions are caused among organs of patients such as movement or rotation defined as rigid motion or entirely deformation, or partial deformation caused by extrusion among patients organs, defined as non-rigid motions. Base on above issues, a method for registering and fusing the ultrasound image with the pre-stored modality image is provided in this embodiment. A breath state model for describing the motion of organs with patient breath is built based on the position indicating information of the position sensor and the ultrasound video data at first. After that, a time-varying correction spatial model acquired through the breath state model is implemented for registering and fusing to reach the purpose for reducing and eliminating of breath-effect.

The method for reducing and eliminating breath effect implemented in this embodiment is described in mathematical formula as:

$$X_{sec} \cdot P \cdot T(R_{probe} \cdot A \cdot X_{us}) \quad (2)$$

T is a kind of spatial mapping algorithm for correcting, selected form linear mapping, affine mapping and other non-linear mapping algorithms. In general, T is defined as a random continuous mapping among algorithm three-dimensions. Specifically, T can be a space mapping matrix for correction.

Generally, breath motion is more regular under free-breathing condition and is able to be defined as a periodic motion approximately. When patient breaths, his abdominal skin mainly moves along with back-forward direction and is defined as a back-forward reciprocating motion approximately. For those target organs that its motions are mainly caused by breath, similar to abdominal skin motions, and its motions are capable of defined as a periodic motion as well. A linear model is implemented to describe motions of this kind of target organs versus breath motion under the condition that motions of this kind of target organs are rigid motions. Linear model is imported for explaining in this embodiment. In those embodiments that motions of this kind of target organs contains non-rigid component, conventional non-rigid algorithm is combined to resolve non-rigid component issue. Regarding to linear model, each point in space shares the same mapping relationship, shown as Formula (3):

$$X_{sec} \cdot P \cdot T \cdot R_{probe} \cdot A \cdot X_{us} \quad (3)$$

Wherein the spatial mapping T degenerates as a matrix.

For the purpose of building the breath model, a breath sensor 109 is implemented into the embodiment shown in FIG. 1. the breath sensor 109 is fixed on the patient's abdominal skin for following the motions of a position the breath sensor 109 fixed on so as to sample how above position moves with patient breath.

For the understanding of following descriptions, relative terminologies are defined below:
(1) Reference position: any position on the motion path of the breath sensor moving with abdominal skin, such as a middle position on the motion path of the breath sensor;
(2) Breath depth: the movement of the breath sensor relative to reference position, implemented for describing the state of breath approximately, defined as d(t). Breath depth is acquirable by referring to the breath position information $R_{resp}(t)$ and implemented through conventional transformation method to transform position information of the breath sensor.
(3) Reference breath depth: reference breath depth is the breath depth relates to the breath depth corresponding to the reference position, defined as $d_0$.
(4) Relative motion amount of reference coordinate system: the position of the target organ under the reference breath depth $d_0$ is defined as the reference position. The motion amount relates to the reference position under different breath depth d(t) in the world coordinate system is defined as relative motion amount of reference coordinate system. For explaining, rigid motion is applied as example in this embodiment and rotation motion is ignored but only relative motions of the reference coordinate system are considered. The relative motion amount of reference coordinate system is defined as W(d(t)) in this embodiment.

Figure 5:
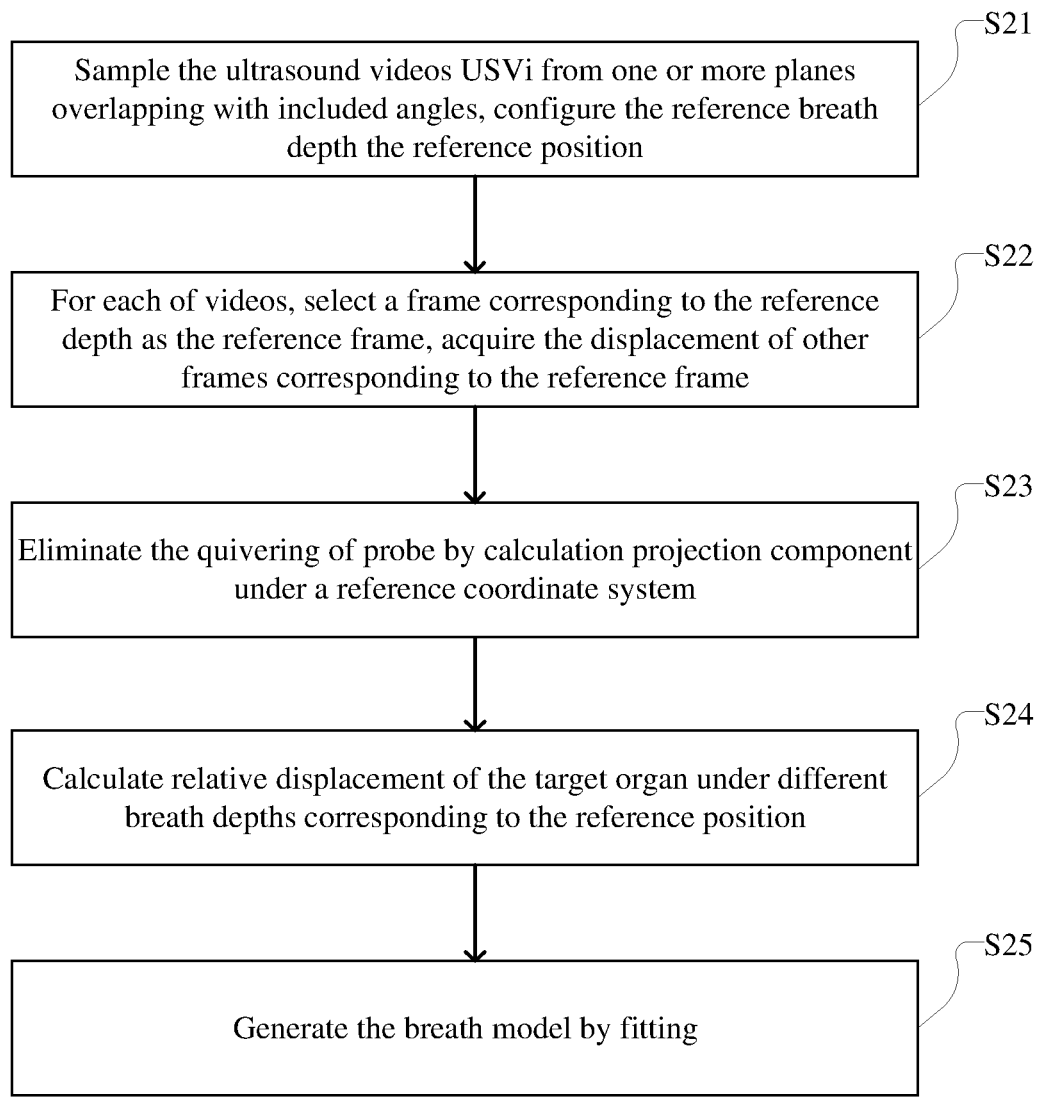
FIG. 5 is a schematic flow chart of a building breath module in accordance with an embodiment of the present disclosure.

As illustrated in FIG. 5, the method for building the breath model in this embodiment comprises below steps S21~S25. Step 21, configuring the reference breath depth and the reference position in accordance with the pre-stored ultrasound video data. Pre-stored ultrasound video data is generated by sampling data for patient abdomen from one plane or multiple planes (such as n planes, n is a positive integer) overlapping each other with included angles, wherein sections of ultrasound video data are sampled from each planes separately. That means one portion of the ultrasound video is sampled from one corresponding plane individually so as to generate n sections of ultrasound video data $USV_i$, i=1, . . . , n, frame numbers of the ultrasound video data presents by variable t. Variable $USV_i(t)$ indicates the t frame ultrasound image in the i portion of the ultrasound video data. In the meantime, the breath position information $R_{resp}(t)$ and the position indicating information $R_{probe}(t)$ in each frame of sampled ultrasound images are recorded. In each sampling process for each ultrasound video, sampling period contains one or more period of breath.

Figure 6:
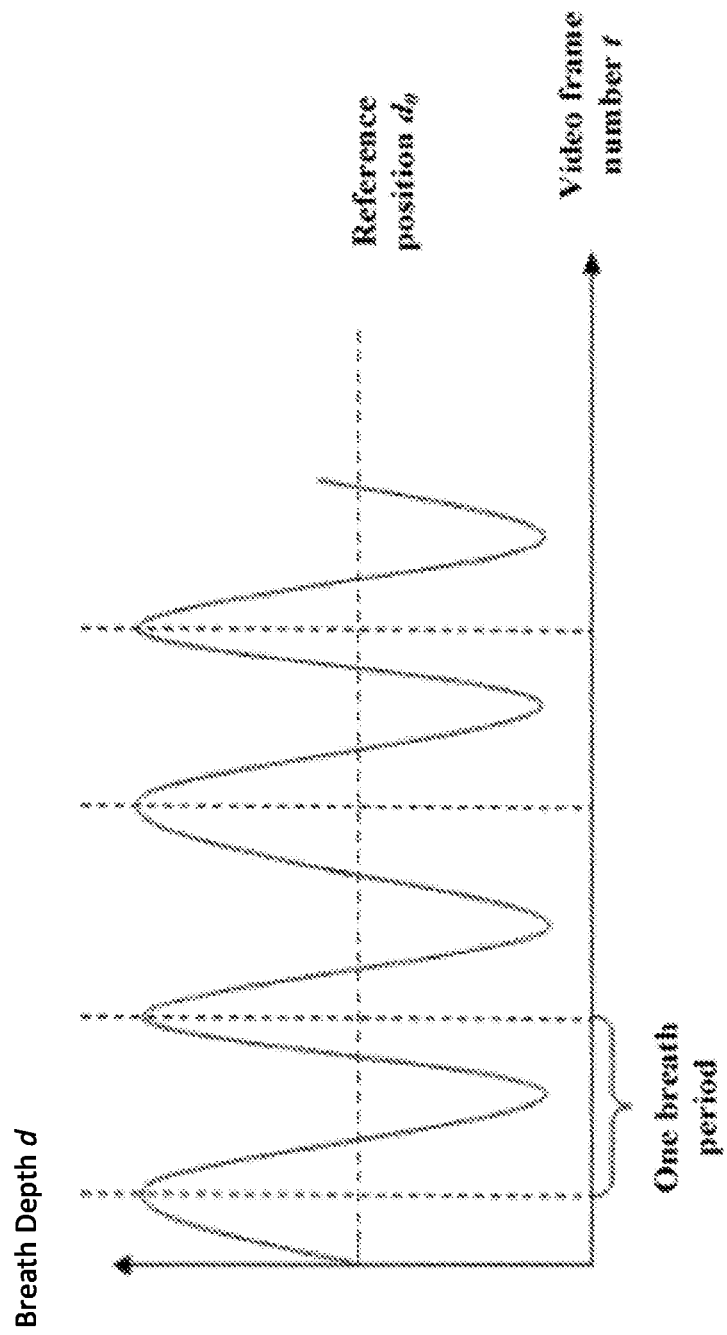
FIG. 6 is a schematic block diagram of a breath depth relating to time axis according to an embodiment of the present disclosure.

As described above, the feature of breath motion is its periodicity. This periodic characteristic is similar with the sine wave shown in FIG. 6. The horizontal axis t indicates breath period, and the vertical axis indicates breath depth d(t). Each repeating curve indicates a breath periodic. As shown in FIG. 6, transverse broken line is defined as the reference position do, and breath depth varies with frame numbers t of video data. The reference position is defined as the middle position in the motion path of the sensor in this embodiment. Apparently, the reference position could be defined as the lowest or the highest position in the motion path of the sensor as well. Since the same breath depth might relates to inhaling state or exhaling state, the breath state could be further distinguishes as inhaling phase and exhaling phase so as to generate sine wave curve similarly.

In step S22, a reference frame is selected corresponding to each portion of video data to acquire motion amount Vi(d(t)) relating to the reference frame for a target object corresponding to other frames of ultrasound image.

For each portion of ultrasound video data $USV_i$, if one frame of the ultrasound image corresponding to breath depth $d_0$ is selected as the reference frame, the motion amount $V_i(d(t))$ relating to the reference frame for a target object corresponding to other frames of ultrasound image is acquired through motion tracing via conventional algorithm such as model mapping algorithm.

Step S23 comprises step that transforming image data into the same reference coordinate system to reduce or eliminate the quivering effect of the ultrasound probe. Since the ultrasound probe is hard to guarantee it's still state for sure when the breath correcting video data is sampled, the motion following process should be conducted only restrict in the plane of the reference frame to eliminate the quivering effect of the ultrasound probe. In step S23, if $x_0$ is the position of one point of the reference frame and $x(t)$ is the mapping position of above position of one point acquired by the motion following process in the t frame of ultrasound image. If $R_{resp}(t)$ is defined as the breath position information and $R_{probe}(t)$ is defined as the position indicating information, the corresponding points of $x_0$ and $x(t)$ are defined as $m_0$ and $m(t)$, then:

$$m_0 = R_{probe\_0} \cdot A \cdot x_0 \quad (4)$$

$$m(t) = R_{probe}(t) \cdot A \cdot x(t) \quad (5)$$

if the projection component of $W(d(t))$ of other frames (not the reference frame) in the plane corresponding to the reference frame is defined as $proj_i(W(d(t)))$, $V_i(d(t))$ is the observed value of the projection component of the projection component $proj_i(W(d(t)))$. Under above configuration, the projection component of $m(t)-m_0$ in the plane corresponding to the reference frame is $proj_i(m(t)-m_0)$. It is the common mathematical function of the observed value $V_i(d(t))$ of $proj_i(W(d(t)))$:

$$V_i(d(t)) = proj_i(m(t)-m_0) \quad (6)$$

In this embodiment, the reference frame and those non-reference frames are both transformed into the same world coordinate system for projecting process so as to eliminate the shift error caused from quivering probe. Device such as probe clip is implemented to fix the position of probe so as to hold the position of the probe as possible. If the patient stays still, the position of the probe could be defined as a constant in sampling process, and $R_{probe}(t) = R_{probe\_0}$, and $V_i(d(t)) = x(t) - x_0$.

In step S24, in accordance with $V_i(d(t))$ acquired in step S22, the relative motion $W(d(t))$ of the target organ corresponding to other frames of ultrasound image in different breath depth is calculated under the same reference coordinate system.

When all sections of video data are configured at the same reference breath depth, presenting as $d(t)=D$, the relative displacement of the target organ corresponding to the reference coordinate system of the reference position is defined as Formula (7) shown below through optimization, wherein $W(D)$ is the corresponding value when the outmost layer $\Sigma$ is configured as its small value:

$$W(D) = \operatorname{argmin}\left(\sum_{i=1}^{n}\left(\sum_{All\, d(t)=D} \|proj_i(W(D)) - V_i(d(t))\|^2\right)\right) \quad (7)$$

Wherein arg min( ) is defined as the function acquiring the smallest value for function in its brackets. Formula (7) is resolved to get displacement $W(d)$ under multiple breath depth $d(t)$.

In step S25, step fitting different breath depths and its corresponding reference coordinate systems is conducted to acquire a breath model.

Above "breath model" is defined as discipline for displacement of the target organ varying with the breath depth. The term "building breath model" is defined as to acquire the mathematical expression of the discipline for displacement of the target organ varying with the breath depth in accordance with the pre-stored ultrasound video data or observation for above discipline.

In this step, point $(d, W(d))$ is fitted in certain way, wherein d is defined as a self-varying value, so that the discipline for displacement of the target organ varying with the breath depth is acquired correspondingly to get the mathematical expression of it.

Differential mode of two vectors is implemented to determined error $\|proj_i(W(D)) - V_i(d(t))\|^2$ between the projections $proj_i(W(D))$ of $V_i(d(t))$ and $W(d(t))$ in the plane i under certain breath depth D in this embodiment. The margin of the error is also could be described in different way, such as $\|proj_i(W(D)) - V_i(d(t))\|$, in other embodiments.

Figure 7:
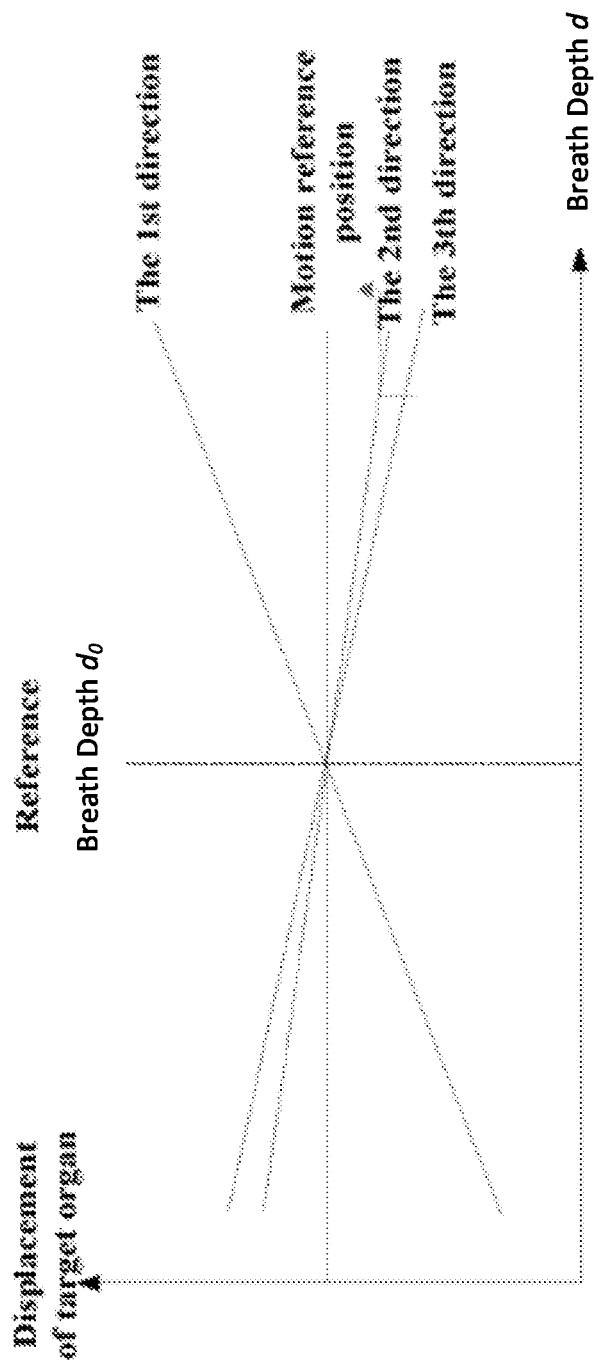
FIG. 7 is a schematic block diagram of the displacement of a target object relating to a reference position through linear fitting with respect to 3 dimensions of the world coordinate system corresponding to change of the breath depth according to an embodiment of the present disclosure.

The schematic diagram of the three straight lines shown in FIG. 7 is the discipline of target organ corresponding to the reference position in three dimensions of world coordinate system with breath depth d. Other fitting methods could be implemented in other embodiments. For example, other curves such as conic curve or cubic curve are also able to be implemented for describing.

In this embodiment, the breath model is implemented for correcting after the breath model is built and before the method disclosed in above embodiment is implemented to register the ultrasound picture with the modality image. In detail, the breath model is implemented to correct different frames of ultrasound images into the same breath depth (the same breath state) so as to reach the purpose for reducing or eliminating the breath effect. The specific correcting process is described below in detail.

If t is one frame of the selected frames selected by doctor for registering, the breath depth corresponding to the frame is $d(t)$, relative displacement of the target organ corresponding to the reference coordinate system of the reference position is $W(d(t))$. If x is one point of the frame, located as $R_{probe}(t) \cdot A \cdot x$ in the world coordinate system, in accordance with Formula (3), the position of the point is transformed as below when it is corrected to the reference breath depth:

$$T(W(d(t))) \cdot R_{probe}(t) \cdot A \cdot x \quad (8)$$

Wherein $T(W(d(t)))$, which defined the breath depth $d(t)$ corresponding to the ultrasound image frame t as self-varying value, is the breath correction matrix corrected under the breath model. In this embodiment, $T(W(d(t)))$ is acquired through the linear compensation of breath effect under breath motion discipline in three dimensions for the relative displacement $W(d(t))$. If $W(d(t))=(W_x(d(t)), W_y(d(t)), W_z(d(t)))$, the breath correction matrix under Homogeneous coordinates is defined as:

$$T((W(d(t))) = \begin{bmatrix} 1 & 0 & 0 & -W_x(d(t)) \\ 0 & 1 & 0 & -W_y(d(t)) \\ 0 & 0 & 1 & -W_z(d(t)) \\ 0 & 0 & 0 & 1 \end{bmatrix} \quad (9)$$

In other embodiments, $T(W(d(t)))$ could be acquired through compensation process after certain processes under the motion discipline in one or more dimensions. Processes under the motion discipline could be selected from non-linear transformation or giving different weights in different dimensions.

In this embodiment, the breath model is implemented before the registering process. The breath model is also able to be implemented after the registering process in other embodiments, such as implemented in the fusion process. If the reference breath depth in registering is $d_0$, it is also capable of conducted real-time correction for breath effect in the fusion process through above built breath model. The correction algorithm is identical with the algorithm correcting different frames into the same breath depth disclosed in above registering process. The relationship between $X_{us}$ and $X_{sec}$ sec in the fusion process conducted after correction is defined as Formula (10):

$$X_{sec}=P \cdot T(W(d(t))) \cdot R_{probe}(t) \cdot A \cdot X_{us} \quad (10)$$

Figure 8:
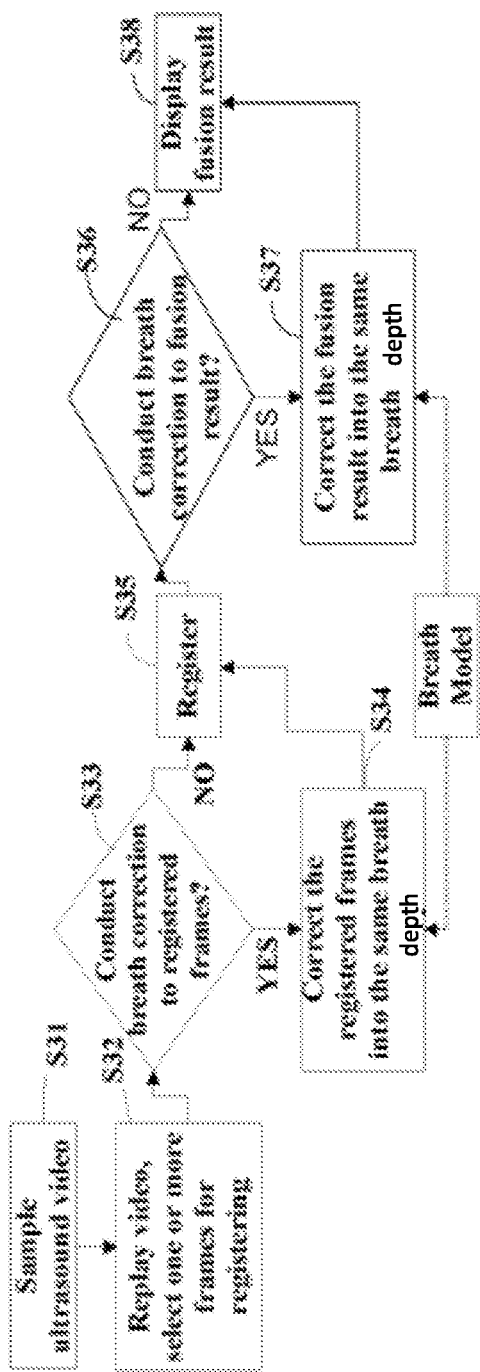
FIG. 8 is a schematic flow chart of a registering and fusing process after the breath module is built according to an embodiment of the present disclosure.

FIG. 8 is a schematic flow chart of registering and fusion processes after breath module is built according to an embodiment of the present disclosure based on ultrasound images, position indicating information of position sensor and position information of the breath sensor. The flow chart shown in FIG. 8 comprises specific steps disclosed below: step S31 for sampling the ultrasound video data, step S32 for replaying the ultrasound video data and selecting one or multiple image frames for registering, step S33 for determining whether or not to conduct breath correction for the registered frames. If it is positive (YES), step S34 is conducted for correcting the registered frames into the same breath depth. If it is negative (NO), step S35 is conducted for registering the selected image frames. In step S36, it is determined that whether or not to conduct breath correction for the fusion result, if it is positive (YES), step S37 is conducted for correcting the fusion result into the same breath depth and he step S38 is conducted thereafter. If it is negative (NO), step S38 is conducted for displaying the fusion result. In the registering step, doctor is able to replay the video for selecting one or multiple ultrasound images for registering and acquire the position indicating information of the position sensor for registering. If the selected multiple ultrasound frames are under different breath depth, it is able to correct the selected multiple ultrasound frames into the same breath depth before the registering step. Alternatively, if doctor wants to observe the fusion result in the same breath depth, it is able to correct it into the depth by implementing the breath model.

In above embodiments for explaining how to correct the multiple ultrasound frames into certain breath depth through the breath model and how to correct the fusion result into certain breath depth, it is assumed that the target depth of the correction object is defined as the reference depth $d_0$ as the breath model is built. However, it is understandable that the correction depth of the target object could be any breath depth, and the breath correction matrix is transformed from $T(W(d(t)))$ to $T^{-1}(W(D)) \cdot T(W(d(t)))$.

A method for fusing at least one ultrasound image with a pre-stored modality image disclosed in this embodiment comprises below steps: a replaying step for playing at least one ultrasound image frame from at least one pre-stored ultrasound video data frame by frame under input instruction or replaying the ultrasound image frame above under input instruction, wherein the ultrasound video data comprises the ultrasound image frame sampled from the target object in at least one plane and position indicating information corresponding to each of the ultrasound image frame, the position indicating information is generated by sensing the position of a position sensor fixed with a ultrasound probe while acquiring the ultrasound image, the breath position information is generated by sensing breath of the target object through the breath sensor fixed on the target object while acquiring the ultrasound image;

a registering step for registering the selected ultrasound image frame with the modality image by implementing the position indicating information corresponding to the selected ultrasound image frame in the registering step, wherein the registering method could be implemented by conventional image registering algorithm; and an image fusing step for fusing the registered ultrasound image frame with the modality image, wherein the multiple ultrasound images are corrected into the same breath depth after registering through the breath model so as to allow doctor to observe the breath depth under the same breath depth.

The implement of how to build the breath model and how to correct images into the same breath has been already disclosed in above embodiments. Therefore, corresponding descriptions related are omitted herein.

A method for fusing at least one ultrasound image with a pre-stored modality image comprises below steps:

selecting multiple ultrasound image frames from at least one ultrasound video data, defined as a selecting step, wherein the ultrasound video data comprising the ultrasound image frame sampled from a target object in at least one plane and position indicating information corresponding to each of the ultrasound image frame, the position indicating information is generated by sensing the position of a position sensor fixed with a ultrasound probe while acquiring the ultrasound image, the breath position information is generated by sensing breath of the target object through the breath sensor fixed on the target object while acquiring the ultrasound image;

building a breath model according to the ultrasound video data, defined as a breath model-building step;

registering the selected ultrasound image frame with a modality image, defined as a registering step; and image fusing the registered ultrasound image frame with the modality image, defied as a image fusing step, wherein the breath-correcting step is conducted in the condition selected from conducting the breath-correcting step before the registering step or conducting the breath-correcting step after the image fusing step.

In one embodiment, a step for building the breath model comprises below steps:

selecting a ultrasound image frame corresponding to a reference breath depth as a reference frame for each portion of the ultrasound video data to acquire a motion amount of the target object corresponding to other ultrasound frames with respect to the reference frame, and calculating a relative motion amount of the target object corresponding to other ultrasound frames in a reference coordinate system under different breath depths, which defined as a relative motion-calculating sub-step; and fitting the different breath depth with the relative motion amount in the reference coordinate system under different breath depths to build the breath model, defined as a fitting sub-step.

In another embodiment, the step of correcting multiple ultrasound frames into the same breath depth further comprises:

for any ultrasound image frame of the multiple ultrasound video, acquiring the breath depth corresponding to the ultrasound frame by implementing the corresponding breath position information and the relative motion amount of the target object in the ultrasound frame under the reference coordinate system of the reference position according to the breath model, which defined as a calculating sub-step; and correcting the relative motion amount in the coordinate system corresponding to the multiple ultrasound frames to a predetermined breath depth according to the breath model, defined as a correcting sub-step.

Detail descriptions of above steps and sub-steps could be referred to corresponding parts in above embodiments and are be omitted herein. The multiple ultrasound image frames processed in the registering step in this embodiment could be selected from the multiple image frames selected when the breath model is built or the multiple image frames acquired based on the real-time ultrasound images.

As described above, for resolving two disadvantages of conventional registration implementations, that are low registering accuracy and fusing success rate based on real-time ultrasounds and poor performance for eliminating breath effect, a registering and fusing method implemented by replaying ultrasound video data with the position sensor information is provided at the present application. A breath model is built for breath correction in the mean time. For conducting breath correction, patient should be asked to breath normally and the ultrasound videos for each of the position overlapping with included angles among each other for more than one breath period is sampled to record sensor position information of the sensor on the probe, indicating information corresponding for each of the ultrasound image frames and breath sensor position information for the breath sensor fixed on patient's abdomen. The patient's breath model is built according to the video and the sensor information hereafter.

Before the registering step is conducted, in the sampled ultrasound video data containing information for registering, each of the ultrasound images contains information of the sensor position information and the indicating information of the sensor fixed with the ultrasound probe and the breath sensor position information for the breath sensor fixed on patient's abdomen. In the registering step, doctor is allowed to replaying the video for searching the video continuously or frame by frame so as to select one or more image frames for registering, and the corresponding position information of the position sensor fixed with the ultrasound probe is acquired for registering by the navigation system at the same time. When the multiple frames are selected for registering, doctor is allowed to correct the multiple frames into the same breath state by implemented the breathe model and the breath sensor information. In the fusion step, the result is corrected in real-time according to the breath sensor information by implemented the breath model so as to reach the purpose of eliminating or reducing the breath effect.

The image fusion method disclosed in the present application registers and fuses the ultrasound video with other modality data and corrects the fusion result with the modality data for breath correction. The image fusion method disclosed in the present application is not only able to be implemented in examination for liver but also able to be implemented in examination for other abnormal organs such as kidney or prostate.

It is understandable for the skilled in the art that all or some of the processes disclosed in the embodiments of the present application are able to be implemented by instructing relating hardware through computer programs. Above programs are able to be stored in a readable storing media of computer. Above programs are able to include the implement of all flow charts for all methods disclosed in above embodiments in execution. The readable storing media include but not limited to select from below: Hard Disc, Optical Disc, Read-Only Memory (ROM) and Random Access Memory (RAM).

Although the present disclosure has been described through specific embodiments, the present disclosure is not limited to the specific embodiments described above. Those of skill in the art should understand that various modifications, alternatives and variations may be made based on the present disclosure, which all should be within the scope of protection of the present disclosure. Furthermore, "a (an) embodiment" or "another embodiment" mentioned above may represent different embodiments, or may also be combined completely or partly in one embodiment.

The invention claimed is:

1. A method for fusing at least one ultrasound image with a pre-stored modality image comprising:
   selecting multiple ultrasound image frames from at least one portion of pre-stored ultrasound video data, defined as a selecting step, wherein the ultrasound video data comprises ultrasound image frames sampled from a target object along at least one plane and a position indicating information corresponding to each of the ultrasound image frames at a sampling period, wherein the position indicating information is generated by sensing a position of a position sensor fixed with an ultrasound probe while sampling the ultrasound image frames;
   registering the at least one selected ultrasound image frame with the modality image, defined as a registering step, by implementing the position indicating information corresponding to the at least one selected ultrasound image frame in the registering step to create a registered ultrasound image; and
   fusing the registered ultrasound image frame with the modality image, defined as an image fusion step;
   building a breath model according to the ultrasound video data, defined as a breath model building step, using the position indicating information corresponding to each of the ultrasound image frames, wherein in each of the ultrasound image frames, a breath depth is defined as a movement of a breath sensor relative to a reference position of the breath sensor, the breath sensor is configured to be fixed on the target object; and
   correcting, using the breath model, the multiple ultrasound image frames to have a same breath depth across the multiple ultrasound image frames in a breath-correcting step occurring at either or both before the registering step and during the fusing step,
   wherein the ultrasound video data further comprises breath position information corresponding to each of the ultrasound image frames, the breath position information is generated by sensing the breath of the target object through the breath sensor while sampling the ultrasound image frames; and
   wherein the breath model-building step comprises:
      selecting an ultrasound image frame corresponding to a reference breath depth at the reference position on a motion path of the breath sensor fixed on the target object as a reference frame for each portion of the ultrasound video data and acquiring a motion amount of the target object corresponding to other ultrasound image frames with respect to the reference frame, and calculating a relative motion amount of the target object corresponding to other ultrasound image frames in a same reference coordinate system under different breath depths, based on the motion amount, defined as a relative motion-calculating sub-step; and
      fitting the different breath depths and relative motion amounts, including the relative motion amount, in the reference coordinate system under the different breath depths to build the breath model, defined as a fitting sub-step.

2. The method of claim 1, wherein the relative motion amount of the target object corresponding to other ultrasound image frames in the reference coordinate system under different breath depths satisfies:

an error between the motion amount of the target object corresponding to the reference frame and the relative motion amount under reference coordinate system at a predetermined breath depth is minimized.

3. The method of claim 2, wherein the motion amount is a rigid motion amount defined as part of a periodic motion, the relative motion amount under the reference coordinate system is an amount of displacement, the relative motion amount of the target object corresponding to other ultrasound image frames in the reference coordinate system under different breath depths is calculated according to the following formula:

$$\underset{W(D)}{\operatorname{argmin}} \left( \sum_{i=1}^{n} \left( \sum_{All\, d(t)=D} (f(proj_i(W(D)) - V_i(d(t)))) \right) \right)$$

wherein the breath depth is d(t), $V_i(d(t))$ is a displacement amount of the target object relating to the reference frame, W(D) is a displacement amount of the target object under the breath depth D, $proj_i(W(D))$ is a projection component of W(D) in a plane corresponding to the reference frame, n is the number of all portions of the ultrasound video data, i=1,... ,n, $f(proj_i(W(D))-V_i(d(t)))$ is an error function of $proj_i(W(D))$ and $V_i(d(t))$.

4. The method of claim 1, wherein the step of correcting multiple ultrasound frames into the same breath depth comprises:
for any ultrasound frame of the multiple ultrasound frames, acquiring the breath depth corresponding to the ultrasound frame by implementing the corresponding breath position information, and acquiring the relative motion amount of the target object in the ultrasound frame with respect to the reference position according to the breath model, which defined as a calculating sub-step; and
correcting, in a breath correction step, the relative motion amount in the coordinate system corresponding to the multiple ultrasound frames to a predetermined breath depth according to the breath model, which is defined as a correcting sub-step.

5. The method of claim 4, wherein the motion amount is a rigid motion amount defined as part of a periodic motion, the relative motion amount in the reference coordinate system is a displacement amount, and the correcting sub-step comprises:
acquiring translation vectors of the target object in each dimension of the reference coordinate system according to the displacement amount;
determining a rotating factor according to the breath model;
acquiring a breath correction matrix according to the translation vectors and the rotating factor; and
correcting the relative motion amount in the reference coordinate system corresponding to the multiple ultrasound frames to a predetermined breath depth according to the breath correction matrix.

6. The method of claim 4, wherein the step of correcting the relative motion amount in the reference coordinate system corresponding to the multiple ultrasound frames to the predetermined breath depth comprises:
for any point on any frame of the ultrasound image frames, calculating a position of the point in the reference coordinate system and calculating a position of the point in the predetermined breath depth using P·T ($R_{probe}·A·X_{us}$), wherein P is a transformation matrix from a ultrasound image space to a modality image space, T is a space mapping matrix for correction, $R_{probe}$ is a transformation matrix from a position sensor space to a world coordinate system, A is a transformation matrix from the ultrasound image space to the position sensor space, and $X_{us}$ is a coordinate of the point in the ultrasound image space.

7. The method of claim 5, wherein the image fusion step after the breath correction step is calculated according to:

$$X_{sec}=P·T(W(d(t)))·R_{probe}(t)·A·X_{us}$$

wherein $X_{us}$ is a coordinate of the point in the ultrasound image space, $X_{sec}$ is a coordinate of the point in the modality image, P is a transformation matrix from a ultrasound image space to a modality image space, T(W(d(t))) is a breath correction matrix, $R_{probe}(t)$ is a transformation matrix from a position sensor space to a world coordinate system, A is a transformation matrix from the ultrasound image space to the position sensor space.

8. The method of claim 1, further comprising:
displaying multiple registered ultrasound image frames or fused ultrasound image frames, and at least one intersection line and included angle among the multiple registered or fused ultrasound image frames at the same time.

9. An ultrasound image fusion navigation system, comprising:
a probe and a position sensor fixed with the probe;
a breath sensor configured to be fixed on a target object;
a sampling unit which samples the target object along at least one plane at a sampling period to acquire at least one portion of pre-stored ultrasound video data comprising information for registering, and recording a position indicating information for each of ultrasound image frames of the pre-stored ultrasound video data, wherein the position indicating information is generated by sensing a position of the position sensor while sampling the ultrasound image frames;
a selecting unit which selects multiple ultrasound image frames from the pre-stored ultrasound video data according to an input instruction;
a registering unit which registers the selected multiple ultrasound image frames with a modality image by implementing the position indicating information of the at least one ultrasound image frame;
a fusion unit which fuses the registered ultrasound image frame with the modality image;
a breath model building unit which builds a breath model according to the ultrasound video data, using the position indicating information corresponding to each of the ultrasound image frames, wherein in each of the ultrasound image frames, a breath depth is defined as a movement of a breath sensor relative to a reference position of the breath sensor;
a correcting unit which corrects, using the breath model, the multiple ultrasound image frames to have a same breath depth across the multiple ultrasound image frames;
wherein the sampling unit further records breath position information corresponding to each of the ultrasound image frames, the breath position information is generated by sensing the breath of the target object through the breath sensor while sampling the ultrasound image frames; and wherein the breath model building unit builds the breath model by:

selecting an ultrasound image frame corresponding to a reference breath depth at the reference position on a motion path of the breath sensor fixed on the target object as a reference frame for each portion of the ultrasound video data and acquiring a motion amount of the target object corresponding to other ultrasound image frames with respect to the reference frame, and calculating a relative motion amount of the target object corresponding to other ultrasound image frames in a same reference coordinate system under different breath depths, based on the motion amount; and fitting the different breath depths and relative motion amounts, including the relative motion amount, in the reference coordinate system under the different breath depths to build the breath model.

* * * * *